United States Patent
Bandy et al.

(10) Patent No.: US 9,974,430 B2
(45) Date of Patent: May 22, 2018

(54) INGESTIBLE ENDOSCOPIC OPTICAL SCANNING DEVICE

(71) Applicant: Innurvation, Inc., Columbia, MD (US)

(72) Inventors: William Robert Bandy, Gambrills, MD (US); Brian Glenn Jamieson, Severna Park, MD (US); Kevin James Powell, Annapolis, MD (US); Kenneth Edward Salsman, Pleasanton, CA (US); Robert Charles Schober, Huntington Beach, CA (US); John Weitzner, Coto de Caza, CA (US); Michael R. Arneson, Finksburg, MD (US)

(73) Assignee: Innurvation, Inc., Glen Burnie, MD (US)

(*) Notice: Subject to any disclaimer, the term of this patent is extended or adjusted under 35 U.S.C. 154(b) by 0 days. days.

(21) Appl. No.: 14/020,110

(22) Filed: Sep. 6, 2013

(65) Prior Publication Data

US 2014/0221742 A1   Aug. 7, 2014

Related U.S. Application Data

(63) Continuation of application No. 12/370,509, filed on Feb. 12, 2009, now Pat. No. 8,529,441.

(60) Provisional application No. 61/028,102, filed on Feb. 12, 2008.

(51) Int. Cl.
*A61B 1/00* (2006.01)
*A61B 1/06* (2006.01)
*A61B 1/04* (2006.01)

(52) U.S. Cl.
CPC ............ *A61B 1/041* (2013.01); *A61B 1/0607* (2013.01); *A61B 1/0684* (2013.01)

(58) Field of Classification Search
CPC ...................................................... A61B 1/041
USPC ............... 600/109, 476, 160, 178, 170, 176
See application file for complete search history.

(56) References Cited

U.S. PATENT DOCUMENTS

| 2,788,390 A | 4/1957 | Sheldon |
| 2,987,960 A | 6/1961 | Sheldon |
| 3,329,074 A | 7/1967 | Gosselin |
| 3,608,547 A | 9/1971 | Sato et al. |

(Continued)

FOREIGN PATENT DOCUMENTS

| EP | 0 973 122 A2 | 1/2000 |
| EP | 1 326 432 A2 | 7/2003 |

(Continued)

OTHER PUBLICATIONS

International Search Report and Written Opinion in re: PCT/US2009/000878, dated May 21, 2009.

(Continued)

*Primary Examiner* — Anhtuan T Nguyen
*Assistant Examiner* — William Chou
(74) *Attorney, Agent, or Firm* — Sterne, Kessler, Goldstein & Fox P.L.L.C.

(57) ABSTRACT

An ingestible scanning device includes, in an embodiment, a capsule housing having a transparent window and sized so as to be ingestible, a photo-sensing array located within the capsule housing, a mirror located within the housing and oriented to direct an image from a surface outside the transparent window to the photo-sensing array, and a light source for illuminating the surface outside the transparent window.

15 Claims, 13 Drawing Sheets

(56) References Cited

U.S. PATENT DOCUMENTS

| | | | |
|---|---|---|---|
| 3,730,175 A | 5/1973 | Fukami et al. | |
| 4,278,077 A | 7/1981 | Mizumoto | |
| 4,703,219 A | 10/1987 | Mesquida | |
| 4,974,076 A * | 11/1990 | Nakamura | A61B 1/05 348/71 |
| 5,010,412 A | 4/1991 | Garriss | |
| 5,131,398 A | 7/1992 | Alfano et al. | |
| 5,528,557 A | 6/1996 | Horn | |
| 5,604,531 A | 2/1997 | Iddan et al. | |
| 9,959,136 | 11/1999 | Hattori et al. | |
| 6,172,789 B1 | 1/2001 | Kino et al. | |
| 6,294,775 B1 | 9/2001 | Seibel et al. | |
| D457,236 S | 5/2002 | Meron et al. | |
| D457,621 S | 5/2002 | Meron et al. | |
| D457,948 S | 5/2002 | Meron et al. | |
| 6,428,469 B1 | 8/2002 | Iddan et al. | |
| D464,425 S | 10/2002 | Meron et al. | |
| D469,864 S | 2/2003 | Meron et al. | |
| 6,563,105 B2 | 5/2003 | Seibel et al. | |
| 6,580,858 B2 | 6/2003 | Chen et al. | |
| 6,584,348 B2 | 6/2003 | Glukhovsky | |
| 6,607,301 B1 | 8/2003 | Glukhovsky et al. | |
| 6,709,387 B1 | 3/2004 | Glukhovsky et al. | |
| D492,403 S | 6/2004 | Iddan et al. | |
| 6,836,377 B1 | 12/2004 | Kislev et al. | |
| 6,855,111 B2 | 2/2005 | Yokoi et al. | |
| 6,856,712 B2 | 2/2005 | Fauver et al. | |
| 6,918,872 B2 | 7/2005 | Yokoi et al. | |
| 6,934,093 B2 | 8/2005 | Kislev et al. | |
| 6,934,573 B1 | 8/2005 | Glukhovsky et al. | |
| D510,139 S | 9/2005 | Gilad et al. | |
| 6,944,316 B2 | 9/2005 | Glukhovsky et al. | |
| D512,150 S | 11/2005 | Iddan et al. | |
| 6,975,898 B2 | 12/2005 | Seibel | |
| 6,984,205 B2 | 1/2006 | Gazdzinski | |
| 7,009,634 B2 | 3/2006 | Iddan et al. | |
| 7,022,066 B2 | 4/2006 | Yokoi et al. | |
| 7,039,453 B2 | 5/2006 | Mullick et al. | |
| 7,104,952 B2 | 9/2006 | Iddan et al. | |
| 7,118,531 B2 | 10/2006 | Krill | |
| 7,119,814 B2 | 10/2006 | Meron et al. | |
| 7,122,001 B2 | 10/2006 | Uchiyama et al. | |
| 7,140,766 B2 | 11/2006 | Glukhovsky et al. | |
| 7,142,908 B2 | 11/2006 | Glukhovsky | |
| 7,160,258 B2 | 1/2007 | Imran et al. | |
| 7,166,537 B2 | 1/2007 | Jacobsen et al. | |
| D543,272 S | 5/2007 | Gilad et al. | |
| 7,251,383 B2 | 7/2007 | Iddan | |
| 7,295,226 B1 | 11/2007 | Meron et al. | |
| 7,316,647 B2 | 1/2008 | Kimoto et al. | |
| 7,319,896 B2 | 1/2008 | Konno | |
| 7,327,525 B2 | 2/2008 | Kislev et al. | |
| 7,347,817 B2 | 3/2008 | Glukhovsky et al. | |
| 7,348,571 B2 | 3/2008 | Ue | |
| 7,559,890 B2 | 7/2009 | Wallace et al. | |
| 7,625,338 B2 | 12/2009 | Gilad et al. | |
| 7,744,528 B2 | 6/2010 | Wallace et al. | |
| 7,801,584 B2 | 9/2010 | Iddan et al. | |
| 7,817,354 B2 | 10/2010 | Wilson | |
| 8,123,679 B2 | 2/2012 | Xie et al. | |
| 8,529,441 B2 | 9/2013 | Bandy et al. | |
| 2001/0035902 A1 | 11/2001 | Iddan et al. | |
| 2001/0051766 A1 | 12/2001 | Gazdzinski | |
| 2002/0032366 A1 | 3/2002 | Iddan et al. | |
| 2002/0042562 A1 * | 4/2002 | Meron et al. | 600/361 |
| 2002/0109774 A1 | 8/2002 | Meron et al. | |
| 2002/0154215 A1 * | 10/2002 | Schechterman | A61B 1/00193 348/51 |
| 2002/0158976 A1 | 10/2002 | Vni et al. | |
| 2002/0165592 A1 | 11/2002 | Glukhovsky et al. | |
| 2002/0168144 A1 | 11/2002 | Chen et al. | |
| 2002/0177779 A1 | 11/2002 | Adler et al. | |
| 2002/0193669 A1 | 12/2002 | Glukhovsky | |
| 2003/0018280 A1 | 1/2003 | Lewkowicz et al. | |
| 2003/0028078 A1 | 2/2003 | Glukhovsky | |
| 2003/0040685 A1 | 2/2003 | Lewkowicz et al. | |
| 2003/0043263 A1 | 3/2003 | Glukhovsky et al. | |
| 2003/0045790 A1 | 3/2003 | Lewkowicz et al. | |
| 2003/0077223 A1 | 4/2003 | Glukhovsky et al. | |
| 2003/0117491 A1 | 6/2003 | Avni et al. | |
| 2003/0139661 A1 | 7/2003 | Kimchy et al. | |
| 2003/0167000 A1 * | 9/2003 | Mullick et al. | 600/424 |
| 2003/0174208 A1 | 9/2003 | Glukhovsky et al. | |
| 2003/0195415 A1 | 10/2003 | Iddan | |
| 2003/0208107 A1 | 11/2003 | Refael | |
| 2004/0027500 A1 | 2/2004 | Davidson et al. | |
| 2004/0073087 A1 | 4/2004 | Glukhovsky et al. | |
| 2004/0092825 A1 * | 5/2004 | Madar | A61B 1/041 600/473 |
| 2004/0109488 A1 | 6/2004 | Glukhovsky et al. | |
| 2004/0122315 A1 | 6/2004 | Krill | |
| 2004/0127785 A1 | 7/2004 | Davidson et al. | |
| 2004/0138532 A1 | 7/2004 | Glukhovsky | |
| 2004/0138590 A1 | 7/2004 | Jensen et al. | |
| 2004/0171915 A1 | 9/2004 | Glukhovsky et al. | |
| 2004/0181155 A1 | 9/2004 | Glukhovsky | |
| 2004/0197267 A1 | 10/2004 | Black et al. | |
| 2004/0199061 A1 | 10/2004 | Glukhovsky | |
| 2004/0210105 A1 | 10/2004 | Hale et al. | |
| 2004/0236182 A1 | 11/2004 | Iddan et al. | |
| 2004/0240077 A1 | 12/2004 | Kislev et al. | |
| 2005/0065441 A1 | 3/2005 | Glukhovsky | |
| 2005/0068416 A1 | 3/2005 | Glukhovsky et al. | |
| 2005/0143624 A1 | 6/2005 | Iddan | |
| 2005/0143644 A1 | 6/2005 | Gilad et al. | |
| 2005/0159643 A1 | 7/2005 | Zinaty et al. | |
| 2005/0171398 A1 | 8/2005 | Khait et al. | |
| 2005/0177026 A1 | 8/2005 | Hoeg et al. | |
| 2005/0185299 A1 | 8/2005 | Kislev et al. | |
| 2005/0266074 A1 | 12/2005 | Zilberstein et al. | |
| 2006/0015013 A1 | 1/2006 | Gilad et al. | |
| 2006/0034514 A1 | 2/2006 | Horn | |
| 2006/0036131 A1 | 2/2006 | Glukhovsky et al. | |
| 2006/0052708 A1 * | 3/2006 | Iddan et al. | 600/476 |
| 2006/0074275 A1 | 4/2006 | Davidson et al. | |
| 2006/0122461 A1 | 6/2006 | Kislev et al. | |
| 2006/0149132 A1 | 7/2006 | Iddan | |
| 2006/0195014 A1 | 8/2006 | Seibel et al. | |
| 2006/0217593 A1 | 9/2006 | Gilad et al. | |
| 2006/0232668 A1 | 10/2006 | Horn et al. | |
| 2006/0238879 A1 | 10/2006 | Togino | |
| 2007/0002135 A1 | 1/2007 | Glukhovsky | |
| 2007/0060798 A1 | 3/2007 | Krupnik et al. | |
| 2007/0078335 A1 | 4/2007 | Horn | |
| 2007/0160367 A1 | 7/2007 | Togino | |
| 2007/0232874 A1 | 10/2007 | Ince | |
| 2007/0255098 A1 | 11/2007 | Wang et al. | |
| 2007/0276184 A1 | 11/2007 | Okawa | |
| 2009/0012357 A1 | 1/2009 | Suzushima et al. | |
| 2009/0326321 A1 * | 12/2009 | Jacobsen | A61B 1/00177 600/109 |
| 2010/0016662 A1 | 1/2010 | Salsman et al. | |
| 2010/0016673 A1 | 1/2010 | Bandy et al. | |
| 2011/0044515 A1 * | 2/2011 | Spyridonos | G06T 7/0012 382/128 |
| 2017/0027427 A1 | 2/2017 | Salsman et al. | |

FOREIGN PATENT DOCUMENTS

| | | |
|---|---|---|
| EP | 1 637 917 A1 | 3/2006 |
| EP | 1 695 662 A1 | 8/2006 |
| EP | 1 707 105 A1 | 10/2006 |
| EP | 1 715 697 A2 | 10/2006 |
| JP | H03-90128 A | 4/1991 |
| JP | 2007-044214 A | 2/2007 |
| JP | 2007-313340 A | 12/2007 |
| WO | WO 02/054932 A2 | 7/2002 |
| WO | WO 02/055984 A2 | 7/2002 |
| WO | WO 02/073507 A2 | 9/2002 |
| WO | WO 02/080376 A2 | 10/2002 |
| WO | WO 02/094337 A2 | 11/2002 |
| WO | WO 03/003706 A2 | 1/2003 |
| WO | WO 03/010967 A1 | 2/2003 |
| WO | WO 2004/014227 A1 | 2/2004 |

(56) References Cited

FOREIGN PATENT DOCUMENTS

| WO | WO 2004/032621 A2 | 4/2004 |
| WO | WO 2004/096008 A2 | 11/2004 |
| WO | WO 2006/003647 A2 | 1/2006 |
| WO | WO 2006/070367 A2 | 7/2006 |
| WO | WO 2007/126246 A2 | 11/2007 |
| WO | WO 2007/126429 A2 | 11/2007 |

OTHER PUBLICATIONS

Extended European Search Report for EP Patent Appl. No. 09711510.9, dated Feb. 9, 2016, 9 pages.
Partial European Search Report for EP Patent Appl. No. 16001902.2, dated Feb. 24, 2017, 8 pages.
Computer-generated English language translation of specification and claims for Japanese Patent Publication No. H03-90128 A, published Apr. 16, 1991, retrieved from https://www4.j-platpat.input.go.jp/, 6 pages.
Extended European Search Report for EP Patent Appl No. 16001902.2, dated Jul. 4, 2017, 15 pages.
Computer-generated English language translation of specification and claims for Japanese Patent Publication No. JP 2007-044214 A, published Feb. 22, 2007, retrieved from https://www4.j-platpat.inpit.go.jp/, 11 pages.
Computer-generated English language translation of specification and claims for Japanese Patent Publication No. JP 2007-313340 A, published Dec. 6, 2007, retrieved from https://www4.j-platpat.inpit.go.jp/, 14 pages.

\* cited by examiner

INGESTIBLE ENDOSCOPIC OPTICAL SCANNING DEVICE

CROSS-REFERENCE TO RELATED APPLICATIONS

The present application is a continuation of and claims benefit to U.S. patent application Ser. No. 12/370,509, filed Feb. 12, 2009, entitled "INGESTIBLE ENDOSCOPIC OPTICAL SCANNING DEVICE," which is incorporated by reference herein in its entirety. The present application also claims the benefit of U.S. Provisional Patent Appl. No. 61/028,102, filed Feb. 12, 2008, which is incorporated by reference herein in its entirety.

BACKGROUND

Field

Embodiments of the present invention relate to optical scanners, specifically optical scanners located on an ingestible endoscopic device Related Art Modern electronic imaging systems typically utilize a two dimensional focal plane array (FPA). However, this requires the use of a single optical lens element with a stop that is circularly symmetrical in two dimensions to focus the image onto all of the imaging FPA. Currently, small imaging systems such as those used in camera pills for biomedical cameras, as well as for security and industrial applications, are limited in resolution by the pixels in their FPA chip. As a result, the current camera pills for gastric intestinal (also referred to herein as endoscopic) examination have a relatively low resolution of, for example, 300×300 pixels. This results in images that provide extremely limited details and cannot be enlarged significantly for improved diagnostic analysis.

These systems are further impaired with the orientation of the array such that the field of view of the camera pill is continuous and fixed. For example, a camera pill may only look down the central axis of the pill and GI tract thereby presenting the center of the field of view as having very little to no useful image data. Additionally, these camera pills typically require extremely wide angle "fish-eye" lenses to image the tissue along the intestinal wall with the result that the images are distorted and non-uniformly illuminated.

Further, use of a fish-eye lens generates images where the information of the condition of the inside wall of the GI tract is only contained in a ring of pixels at the peripheral region of the image. In this situation the center region of the image shows a view down the length of the intestine and contains little or no useful information. This results in images where the most important data is presented on a small fraction of the pixels in a focal plane imaging array such as a CCD or CMOS imager. This reduction in the effective resolution is exacerbated by the presentation of the image in a distorted circular appearance with the most outer edge visible being brightly lit and close to the imaging array while the rest of the intestinal wall surface is progressively further away from the camera and progressively dimmer in illumination.

Additionally, the images of interest to a physician are images of the intestinal wall, not the forward-looking view down the GI tract. The ability to scan the intestinal walls is thus preferred over traditional camera pill imaging. The ability for the capsule to image the entire tubular wall and the size and electrical connections required for the focal plane array define that the image array be set so that the imaging surface is perpendicular to the axis of the pill.

SUMMARY

An ingestible scanning device includes, in an embodiment, a capsule housing having a transparent window and sized so as to be ingestible, a photo-sensing array located within the capsule housing, a mirror located within the housing and oriented to direct an image from a surface outside the transparent window to the photo-sensing array, and a light source for illuminating the surface outside the transparent window.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
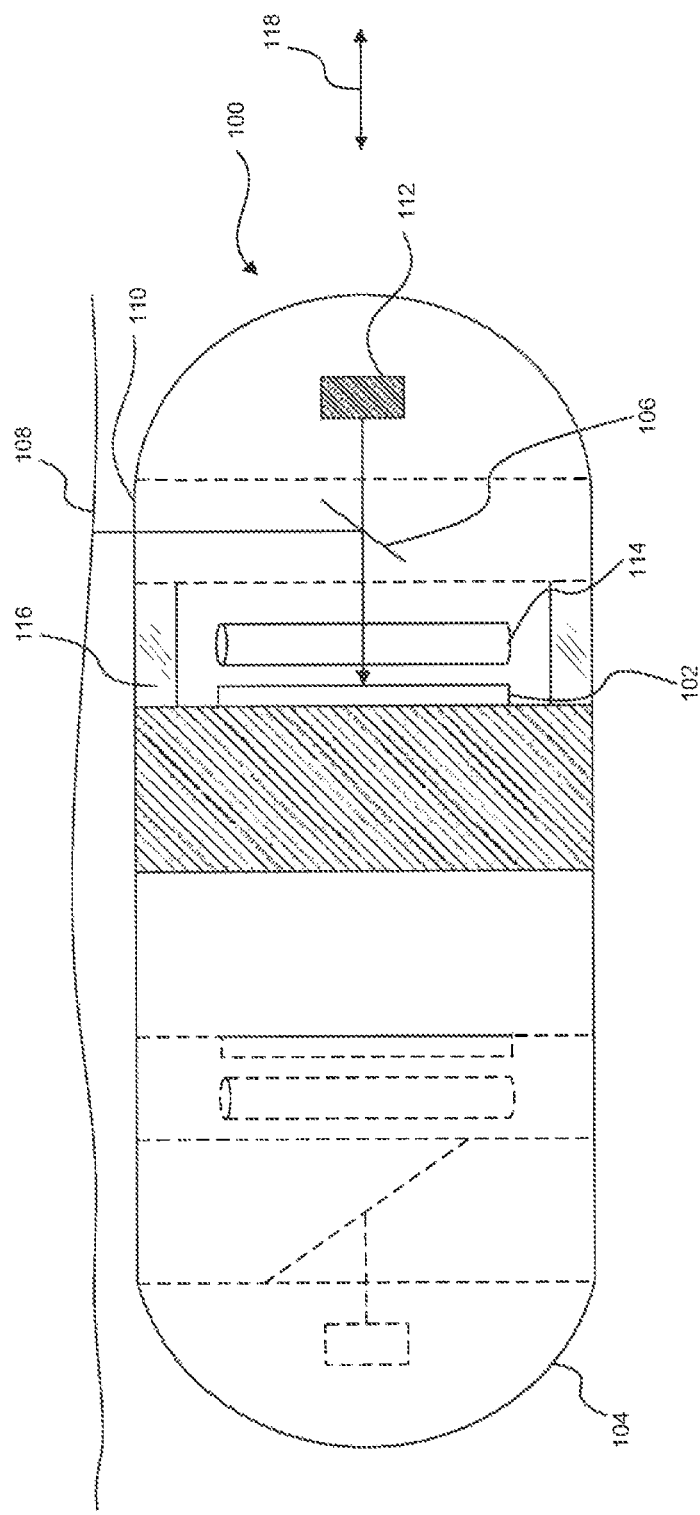
FIG. 1 illustrates an ingestible scanner according to an embodiment of the present invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described.

An ingestible sensor device may be swallowed by a patient, such as a human, to diagnose one or more conditions of the patient. The ingestible sensor device may include a sensor configured to receive a stimulus inside the gastrointestinal tract of the patient, wherein the sensor is configured to output a signal having a characteristic proportional to the received stimulus. The ingestible sensor device may further include a communications module that transmits an acoustic signal modulated with the sensor output signal and a housing configured to have a size that is swallowable, wherein the housing substantially encloses the sensor and communications module. The patient using the ingestible sensor devices may be any type of animal, including a human. In addition, these same sensor devices may be temporarily implanted into patient for the purpose of continuous monitoring, such as with a several hour to several day diagnostic period at 'home' or at a professional care center. A sensor link module may be located on the surface of the patient to receive the acoustic signal output by the sensor. An example ingestible sensor is further described in U.S. patent application Ser. No. 11/851,221, filed Sep. 6, 2007, and U.S. patent application Ser. No. 11/851,214, filed Sep. 6, 2007, each of which is incorporated by reference herein in its entirety.

An ingestible sensor device may benefit from an optical scanner coupled to the ingestible sensor device. Although the present invention will be described with respect to an ingestible endoscopic sensor device, one of skill in the art will recognize that an optical scanner as described herein may be coupled to any type of ingestible device, or may be used on its own, without departing from the spirit and scope of the present invention. Scanned image data from the ingestible sensor device may be transmitted outside the body through use of acoustic data transmission, or using any other type of data transmission known to one of skill in the art. Additional embodiments and features of a radial scanner that may be used in conjunction with the present invention are described in U.S. Prov. Patent Appl. No. 61/030,453, filed Feb. 21, 2008, which is hereby incorporated by reference in its entirety. Additionally, although the present invention is described in conjunction with scanning inside the gastrointestinal tract, one of skill in the art will recognize that a similar scanner may also be used inside vasculature, urinary tract, reproductive tract, lung, nasal or internal ear cavity, or any other cavity of an animal as also described in U.S. Prov. Patent Appl. No. 61/030,453.

Unlike typical camera pills, in an ingestible endoscopic scanner, the need for a focal plane to generate a two dimensional image can be eliminated by the use of a single axis or single element photo-sensor that is coupled with an optical scanning element or is physically scanned over the desired field of view. Whereas the image taken by a focal plane array is simultaneous over the entire field of view and must be scanned out to a memory for transmission, the single axis sensing array is capable of being read a line at a time. With the combination of a scanner, a broadband source, and a linear array, a point-by-point spectrum can be produced using diffractive optics.

The scan line images may be generated without the two dimensional circular lens and stop element used in existing ingestible cameras. In this manner, the single line array of pixels can scan a region such that in one axis, the linear line array provides the resolution while in the opposing axis a scanning system is utilized. In this manner, as will be described further below, the scanning element can be composed of any of a variety of opto-mechanical configurations composed of, for example, an oscillating mirror, a prism, a cylindrical lens, etc. This allows the achievable resolution of the scanned axis and the speed of imaging to be adjustable. Also, this scanning approach can be used with illumination or in combination with a joint illumination and imaging optical configuration producing a highly efficient optical imaging system. In embodiments, this construction may lead to the pixel area on the surface being imaged being defined by the spot size generated by the light source. Color images can be generated either by sequential scans with switching color light sources, or by using pixel rows on the photosensor array each with a color filter assigned to each row.

FIG. 1 illustrates an exemplary ingestible scanner 100 according to an embodiment of the present invention. A single axis photo-sensing array 102 is located such that it extends across the diameter of a capsule housing 104 and is perpendicular to the axis of the capsule and the axis of housing 104. Array 102 may be, for example and without limitation, a single photosensing diode (also referred to herein as a photosensor or photodetector) or a one-dimensional array of multiple photosensors. Housing 104 may be, for example, a tubular housing. A mirror 106 within the pill is placed such that it is at an angle to array 102 that allows array 102 to view the intestinal wall surface 108 through the side wall of housing 104 through a clear aperture 110 in housing 104. Mirror 106 may be, for example, an elliptical mirror. Alternatively, mirror 106 may be a rectangular mirror that deflects on only one axis. Mirror 106 may be placed at an angle of, for example, 90 degrees to array 102. Mirror 106 may be a two-sided mirror, to capture twice the data in a single revolution. Aperture 110 may extend for 360 degrees around housing 104. Mirror 106 may be coupled to a micro-motor 112 such that an electrical signal causes mirror 106 to rotate. The axis of rotation of mirror 106 is approximately parallel to the axis of capsule 100. The rotation of mirror 106 results in array 102 scanning, in a 360 degree field, the region surrounding capsule 100. In an alternative embodiment (not shown), mirror 106 may be attached to a rod having two conductors and suspended in an electrical coil, such that the rod rotates as electricity is applied to the coil.

In an embodiment, a cylindrical lens 114 is placed over array 102 to focus light from surface 108 reflected by mirror 106 onto array 102. Because array 102 is imaging surface 108 through aperture 110 on the side of capsule 100, rather than through the end of capsule 100, resolution of array 102 is approximately uniform at any given scan rate. Resolution may be increased in the rotational axis by adjusting the speed of rotation of mirror 106.

Array 102 is used to generate one or more images of surface 108 by scanning. This is accomplished in one embodiment by moving cylindrical lens 114, which is placed down the length of array 102 such that the curvature of cylindrical lens 114 is perpendicular to the length of array 102. Scanning of the region to be imaged (such as surface 108) is achieved by movement of the relative position of cylindrical lens 114 to array 102. In an embodiment, either of array 102 or cylindrical lens 114 can be moved. In this manner, light from different regions of the image are focused sequentially onto the pixels of array 102 as the movement occurs. By use of cylindrical lens 114 (or a more complex lens surface, in an embodiment) extremely wide angle images can be achieved on the axis of the image that is scanned.

In an embodiment, cylindrical lens 114 is replaced with a scanning mirror or prism. The prism may have either a transmissive or reflective function depending upon the scanning optical design.

Illumination of the imaged wall region, such as surface 108, may be accomplished by placing LED light sources adjacent to array 102, to create a light distribution ring, or "light pipe" 116. In an embodiment, light pipe 116 evenly outputs light around approximately the entire perimeter of housing 104. In an embodiment, light from light pipe 116 is output at multiple frequencies. In this manner individual scans or frames of different frequencies can be captured and integrated into full color images, partial color images or false color images. Light sources may include, for example and without limitation, narrow band emitters in the visible range, white light emitters, ultraviolet emitters and infrared or near infrared emitters. Imaging arrays comprising, for example, three rows of photo-sensors, each with a specific color filter, may be used to generate full visible color images. In this manner the imaging system can be utilized to detect reflection differences in tissue over a spectral range far exceeding the abilities of the human eye. In an embodiment, a pixel size of array 102 may be controlled through the use of mechanical shutters or a shutter wheel. The shutter wheel may include one or more color filters.

In an embodiment, light pipe 116 is located within housing 104. In another embodiment, light pipe 116 is external to housing 104. In an embodiment where light pipe 116 is located external to housing 104, light pipe 116 acts to space the scanning optics off the intestinal wall. Further, positioning light pipe 116 outside housing 104 ensures that the light source path is separated from the received light path, with no internal reflecting surfaces.

Figure 2A:
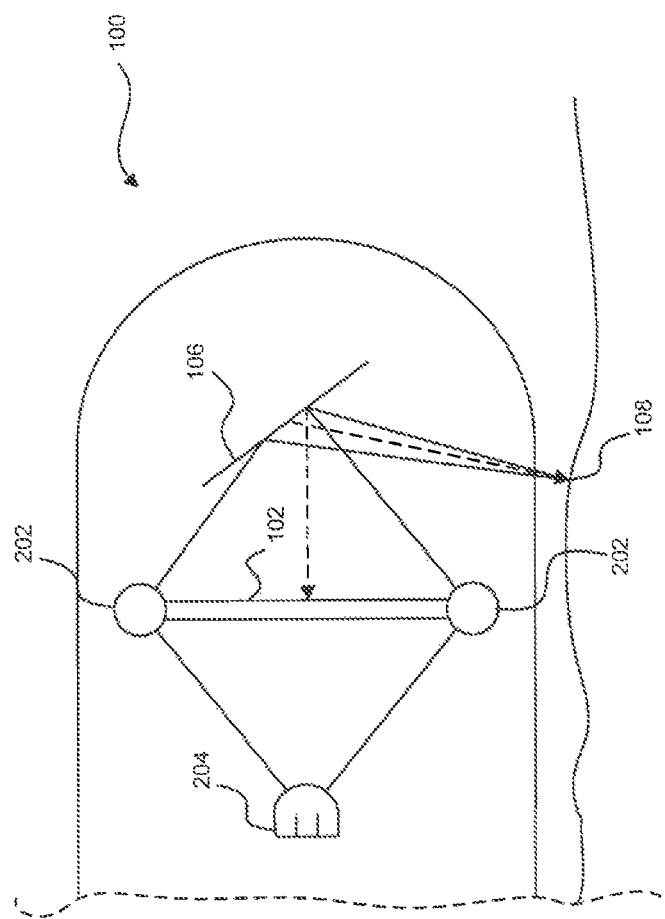
FIGS. 2A and 2B illustrate a lighting system for use in an ingestible scanner, according to an embodiment of the present invention.
Figure 2B:
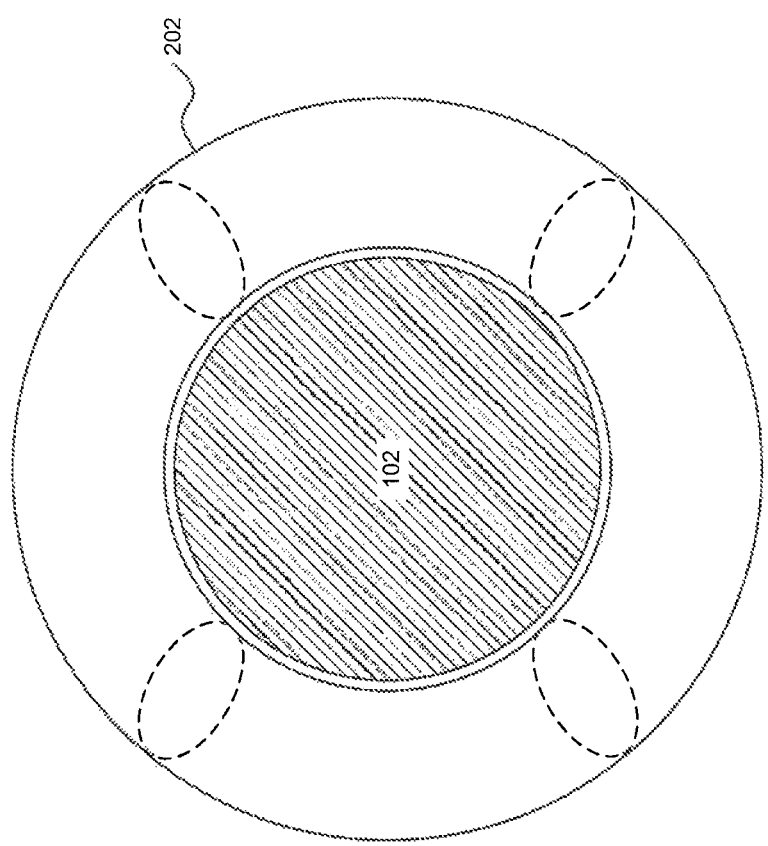

In one embodiment, the entire light pipe 116 may be illuminated at a given time, providing illumination for the entire circumference of the intestinal wall at the same time. In another embodiment, in order to preserve power, light pipe 116 may direct light only to the portion of surface 108 being imaged at a given time by array 102. FIGS. 2A and 2B illustrate an exemplary lighting system for focusing illumination light on intestinal wall surface 108. FIG. 2A illustrates a cross-sectional view of the directional lighting system. As shown in FIG. 2A, a toroidal lens 202 surrounds array 102. The relationship between toroidal lens 202 and array 102 is further illustrated in FIG. 2B. Returning to FIG. 2A, toroidal lens 202 directs illumination light from light source 204 (which may be, for example, an LED) to mirror 106. Mirror 106 further focuses the illumination light onto surface 108. Mirror 106 may be positioned such that surface 108 is approximately located at a focal point of mirror 106. Alternatively, a collimating lens (not shown) may be included between surface 108 and mirror 106 to account for any focal length variability of surface 108. An image from surface 108 is then returned to array 102.

Alternatively, illumination may be provided to a small portion of surface 108 using an optical fiber to direct the illumination light accordingly. In yet another alternative, a photosensor in array 102 may include a hole that allows light to pass through array 102 to mirror 106, and then be reflected onto surface 108.

Illuminating only a small portion of the surface preserves power in the ingestible capsule, because light produced by the light source is focused onto a specific spot rather than distributed across many spots. This allows the amount of radiation output by the light source to be decreased without changing the radiation per pixel received.

Illuminating a small portion of a surface also allows image processing of the imaged surface such that very accurate colorimetry measurements may be made, according to an embodiment of the present invention. Color information may be obtained through use of an array having more than one photodetector element, such as a two- or four-element array. In one embodiment, the array may be separated into subcategories of traditional red, blue, and/or green. Alternatively, a single photodetector element may be used with multiple color light emitting diodes (LEDs), as use of a single photodetector element maximizes the sensitivity of the aperture size. This allows inspection of tissue for regions which have a slight loss of oxygen or are just becoming infected or inflamed. This technique provides higher accuracy of these conditions than that capable with white light and the human eye.

In an embodiment, the illumination intensity can be varied for different views. For example, illumination intensity may be increased when scanning points of particular interest, such as a surface of the intestinal wall. Similarly, illumination intensity may be decreased when scanning across points of lesser interest, such as down the intestine where less light will be reflected back to the detector.

Returning to FIG. 1, the scan rate, as determined by the rotational rate of mirror 106, may be adjusted to match a desired frame rate. This requires less memory and allows more flexibility of the imaging rate. The ability to scan the image with an optical mechanical device also allows the elimination of a complex lens. Although FIG. 1 illustrates mirror 106 as coupled to motor 112 for rotating mirror 106, scanning can alternatively or additionally be accomplished by moving array 102, tilting mirror 106 to view 360 degrees around the sides of capsule 100, or by moving cylindrical lens 114 to scan a region. The rate of motion of array 102, mirror 106, or lens 114 defines the rate of the scan in one axis. For example, mirror 106 may not only be rotatable around a capsule axis 118, but it may also be tiltable, having a pivot line perpendicular to axis 118. Such a tiltable, rotatable mirror provides a two-axis range of motion of mirror 106.

In an embodiment, light pipe 116 homogenizes the intensity and converts the light into a ring which illuminates the optical scanning region with a highly uniform ring of light. In a specific example, not intended to limit the present invention, mirror 106 is oriented at 45 degrees with respect to array 102. Motor 112 rotates mirror 106 and a lens is placed so that array 102 images a 0.5 degree instantaneous field of view. The start of each scan line may be identified by the use of an occlusion in the field of view, such as wires attaching array 102 to its supporting electronics. In this specific example, the system provides approximately 720 pixels per scan with a pixel size of 55 microns. In this example, data may be captured at 16 bits per color giving a 48 bit full color data per pixel. In this example, scan rates may vary from, for example, 1000 rpm to 10,000 rpm. This provides an example resolution of 720×405 pixel full color image comprising 875,000 pixels, which is approximately ⅓ the resolution of a high-definition television. In another example, the axial scan may include a full 720 pixel resolution of 720×1280 pixels.

In an embodiment, the scanner may use feedback from other sensors in the capsule to enter into a single color mode when a full color scan is not substantially different from a previous scan. Similarly, the scanner may enter into a multi-color mode (using two or more colors) when a single color scan is different from previous scans. In another embodiment, such color selection instructions may be received from an operator external to the capsule instead of other sensors within the capsule.

Various additional embodiments are possible using tilting and/or rotating mirrors and/or arrays. As shown in FIG. 1, a second optical system may be located on the opposite end of capsule 100 from array 102 and mirror 106. This allows a 360 degree field of view for capsule 100. FIGS. 3-7 each illustrate a different exemplary configuration for capsule 100.

Figure 3:
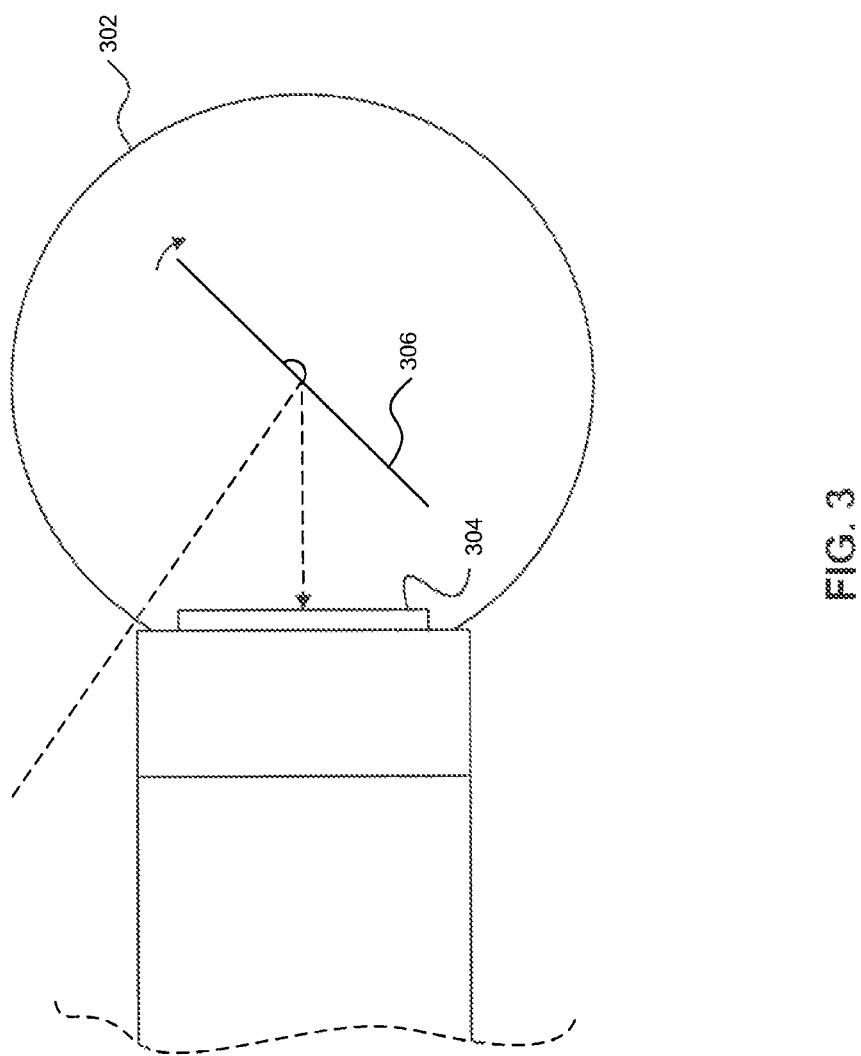
FIG. 3 illustrates an exemplary endcap of an ingestible scanner, according to an embodiment of the present invention.

In FIG. 3, the end of capsule 300 containing the imaging optics includes a globe-shaped housing 302. This allows a very wide angle field to be imaged by photodetector 304.

Figure 4:
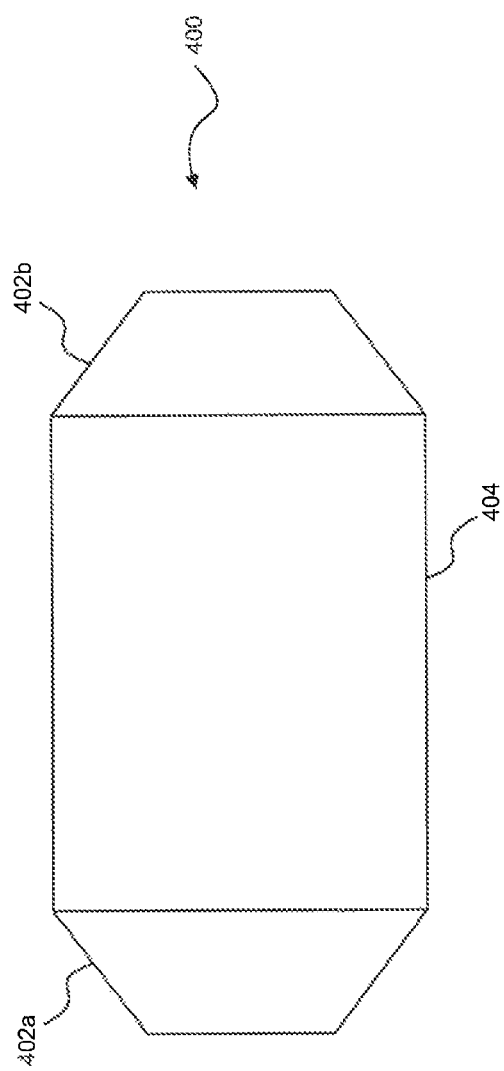
FIG. 4 illustrates additional exemplary endcaps of an ingestible scanner, according to an embodiment of the present invention.

In FIG. 4, ends 402a and 402b of capsule 400 are shaped like a truncated cone, so that light enters the imaging optics through a flat surface. This increases the simplicity of optics required to counteract distortion caused by light passing through housing 404.

Figure 5:
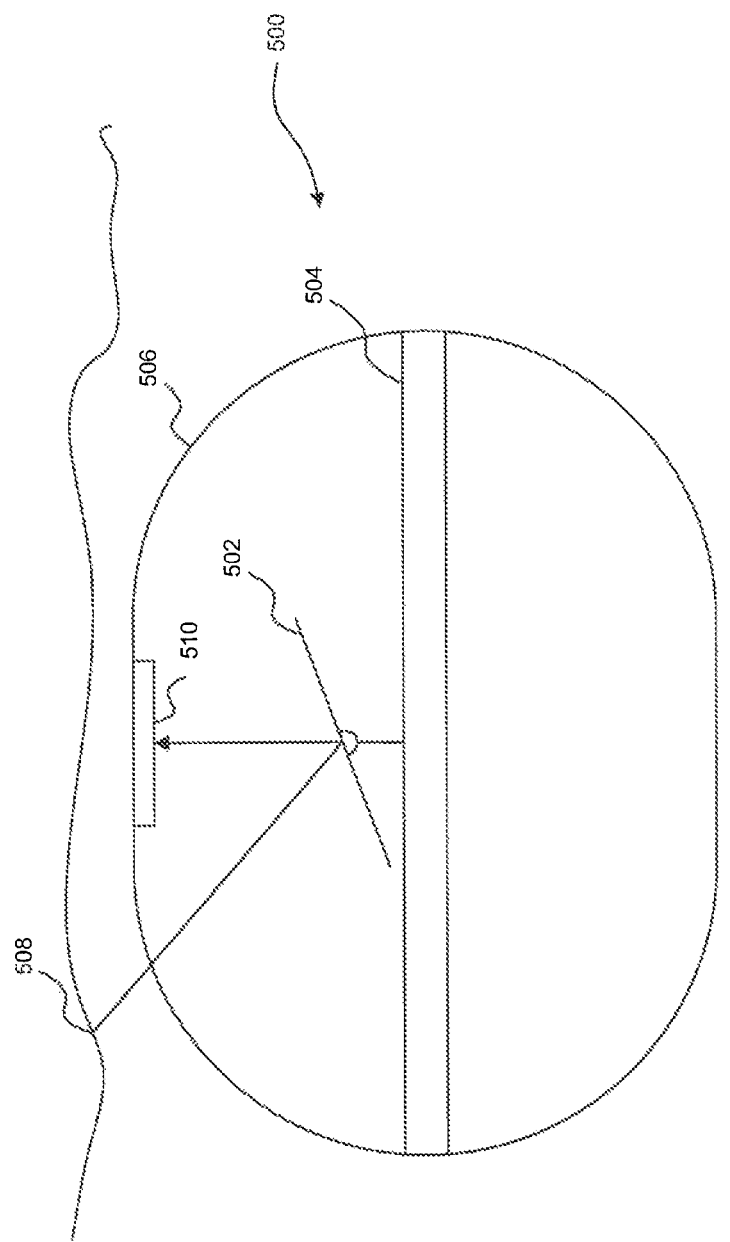
FIG. 5 illustrates a cross-section of an ingestible scanner according to an embodiment of the present invention.

FIG. 5 illustrates a cross-section of a capsule 500, wherein the imaging optics are not located at the ends of the capsule, but instead are located in the central portion of the capsule. Mirror 502 is located on a central cylinder 504. At least a portion of housing 506 is transparent, such that an image from intestinal wall surface 508 is reflected by mirror 502 to photodetector 510. Central cylinder 504 may be rotatable, such that mirror 502 can image around the full perimeter of capsule 500. In an embodiment, mirror 502 is a dish mirror to direct light to photodetector 510 when mirror 502 is tilted. In an embodiment, central cylinder 504 includes an illuminator. The illuminator may be located inside central cylinder 504 with light exiting through a slit in central cylinder 504 (not shown) in order to illuminate intestinal wall surface 508.

Figure 6:
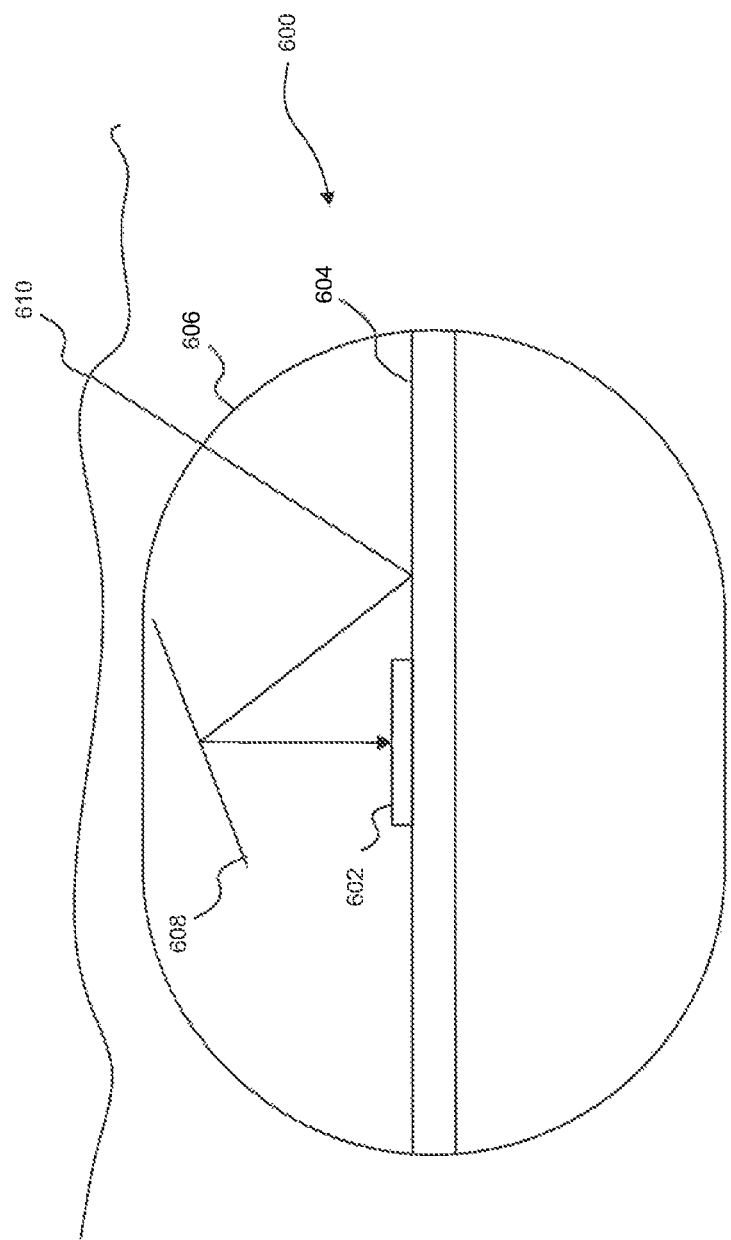
FIG. 6 illustrates a cross-section of another ingestible scanner according to an embodiment of the present invention.

FIG. 6 illustrates a cross-section of a capsule 600, wherein the imaging optics are located in the central portion of the capsule. In this embodiment, photodetector 602 is located on a central cylinder 604. Central cylinder 604 may be made from a reflective material, such that an image from intestinal wall surface 610 enters through transparent housing 606 and reflects off central cylinder 604 to a mirror 608. The image is further reflected by mirror 608 to photodetector 602. Central cylinder 604 may be rotatable, such that photodetector 602 can image around the full perimeter of capsule 600.

Figure 7:
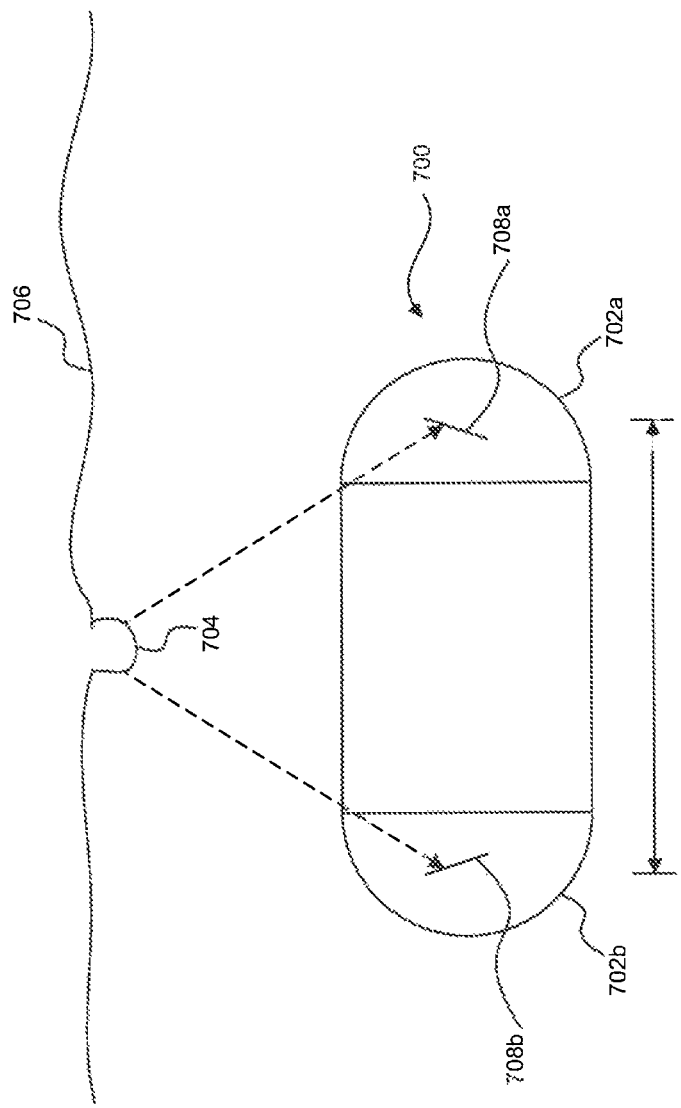
FIG. 7 illustrates a cross-section of another ingestible scanner according to an embodiment of the present invention.

FIG. 7 illustrates a cross-section of a capsule 700, wherein the imaging optics are surrounded by hemispherical lenses 702a and 702b on either end of capsule 700. In an embodiment, hemispherical lenses 702a and 702b may be organized in conjunction with a pre-distorted lens to scan a respective hemisphere of the GI tract with high resolution on the side walls and graduated lower resolution toward the centerline of the scanner field of view.

Figure 11:
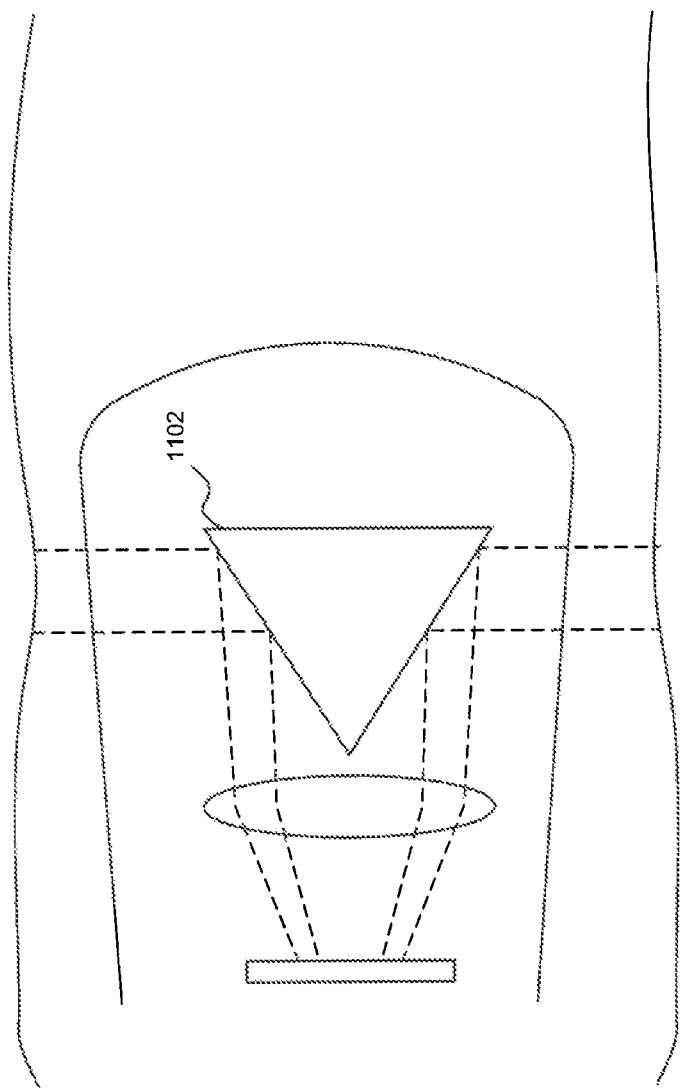
FIG. 11 illustrates an exemplary reflective element according to an embodiment of the present invention.
Figure 12:
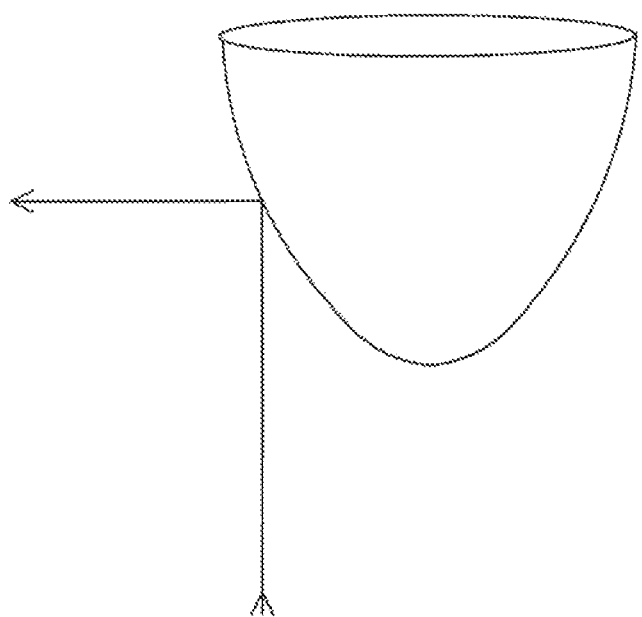
FIG. 12 illustrates another exemplary reflective element according to an embodiment of the present invention.
Figure 13:
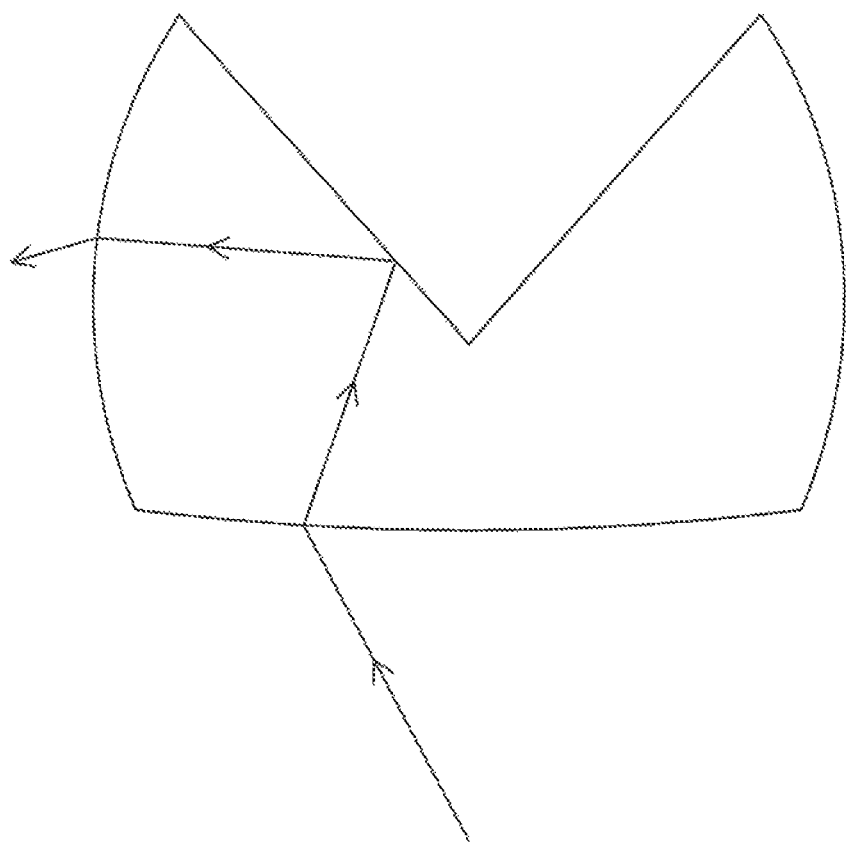
FIG. 13 illustrates an exemplary reflective and refractive element according to an embodiment of the present invention.

In an embodiment where a 2 dimensional photodetector array is used, a conical reflector 1102 may be oriented along the center axis of the optical lens system, as illustrated in FIG. 11. In a similar embodiment, a parabolic mirror or other cylindrically symmetrical reflector, as illustrated in FIG. 12, may be used in place of the conical reflector. In still another embodiment, this mirror element may be composed of one or more reflective and refractive surfaces, as illustrated in FIG. 13. An image may be taken of the inside of the GI tract that maximizes the number of pixels in an imaging array that present a useful image of the internal wall. In addition, illumination of the wall perpendicular to the orientation of the scanner presents a field of view with the tissues at nearly a constant distance from the scanner lens. This improves the ability to capture scan images at a uniform focus, resolution and illumination intensity.

In this embodiment, the conical reflector is designed to match the field of view of the lens and deflect the image into a circular band that is centered at or near 90 degrees to the original axis of the lens. In this manner the lens is provided with an image region where optical path lengths from one edge of the cylindrically imaged region are approximately equidistant to the path length of the opposing edge of the imaged region. A moderate field of view may thus be obtained with a normal lens. This allows simple optical elements to be used with minimal focal or distortion issues. Nearly all the pixels within the imaging array are presented with useful information. This maximizes the usable resolution in the resulting image. It is also easier to illuminate the imaged region in a near uniform manner. The images may then be processed to remove the circular distortion and produce panoramic images that represent an unwrapped and undistorted image of the interior wall.

Another embodiment whereby effects of a variable focal distance are mitigated includes changing the focus position of the lens to bring any specific distance of the imaged surface into focus. Oscillating the focus from a close position to a distant position creates a temporally focused image. This approach can then be used to determine the distance between any region of the imaged surface and the lens. By further incorporating software that can selectively capture regions of the image when they are in focus, it is possible to generate a composite image where the entire image is in focus or to generate a depth map of the surface. Once a depth map of the surface is created, additional image processing can provide a parallax calculation to be made, and images can thereby be created which represent the surface in three dimensions.

More particularly, the distance between the imaging lens and the film or image sensing array (such as a CCD or CMOS focal plane array) may vary depending upon the distance at which the imaged surface is in focus. This results in the spacing of the lens varying as various distances of the imaged surface are brought into focus. By smoothly oscillating the lens between its minimal and maximum spacing above the film or imaging array, it is possible to generate a series of images or frames where each surface region is progressively brought into focus from the closest to the farthest from the lens. Sharp objects or markings on the surfaces which represent high contrast regions (such as edges of shadows or sharp edged color differences) are sharp and high contrast only when they are in focus. The contrast of these objects drops rapidly when the lens position is changed even slightly. In this manner, it is possible to utilize software that analyzes pixel values and identifies adjacent pixels having sharp intensity variations when the lens is in other spacing positions. By capturing these regions in a sequential manner, it is possible to generate a composite image where the entire image surface is presented in sharp focus. The lens spacing information corresponding to each image may be used to create a depth profile map of the surface. This profile may then be used to generate a pseudo three dimensional image by generation of images representative of a parallax pair of images, where the position of near field surfaces is shifted more than the background surfaces.

By utilizing image processing algorithms that capture regions of an image at their highest contrast and incorporating a rapidly dynamic focusing lens system that has a narrow depth of field, the focus position may be used to generate a depth profile of the image. This depth profile may then be utilized to generate a topographic map of the imaged region. The depth profile can additionally be utilized to generate a pseudo-parallax perspective of the imaged region and present the processed image in three dimensions utilizing head-mounted stereoscopic displays or other similar devices. In addition, distortions to the image may be created to enhance the representation of depth on a single display monitor.

This allows presentation of a fully focused image of tissues which vary greatly in distance from the imaging lens, while utilizing an optical lens system designed for the highest light efficiency possible. In addition, the ability to generate depth profiles and pseudo three dimensional images can assist a physician in visualizing the relative position of the tissues, further assisting in diagnosis.

In another embodiment, a scanner having multiple photodetectors in its array enables not only spot detection but also the level of light diffused from the coherent signal sent out. The diffusion may be important, because rough tissue scatters light much more than smooth tissue. Having multiple photodetectors in the array not only offers a gain advantage in that it is more sensitive to reflected light, but it also offers an opportunity to determine a relative amount of light in the center of the image versus the outside of the image, and gives an approximate correlation to smooth tissue as opposed to rough tissue.

As has been discussed, an ingestible optical scanner may include a tiltable and/or rotatable mirror for capturing a wide angle field of view. In an embodiment of the present invention, as introduced with respect to FIG. 1, a capsule may contain two scanning systems, one on each end of the capsule. As discussed above, FIG. 7 is an illustration of an exemplary capsule 700 having scanning optics located in two hemispherical lenses 702a and 702b. Depending on the field of view, it may be possible for each scanning system 702a and 702b to image the same feature 704 on an intestinal wall surface 706. Because of the effects of parallax caused by the distance d separating optics 708a and 708b, a three-dimensional image of feature 704 may be obtained. Although this three-dimensional feature is described with respect to hemispherical lenses 702a and 702b, one of skill in the art will recognize that any type of lenses may be used without departing from the spirit and scope of the present invention.

In another embodiment, a single scanning system may image a feature such as feature 704 from two different locations within the GI tract. In this embodiment, parallax due to the distance between the two locations may be used to provide a three-dimensional image of the feature.

Figure 8:
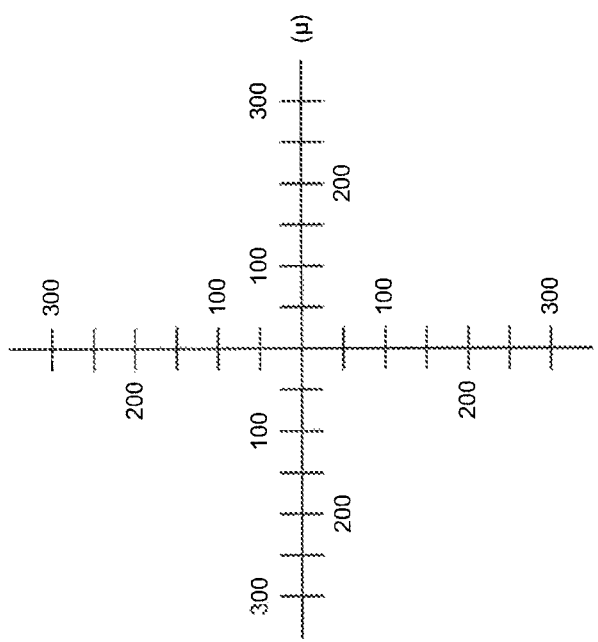
FIG. 8 illustrates exemplary scribes used in an embodiment of the present invention.

In an embodiment of the present invention, the mirror used to reflect images to the capsule's imaging sensor may have scribes located on the mirror's surface in predetermined equal distances from each other. An example set of scribes is illustrated in FIG. 8. Although FIG. 8 illustrates the distance between scribes in terms of micrometers, the distance between scribes could alternatively be fractions of mm, fractions of an inch etc. This provides accurate reference dimensions to aid a physician in identifying size of objects in view on the picture. The scribes on the mirror may result in pictures having the scribe lines always showing as a reference on each and every frame.

The mirror may also be a magnifying mirror, where the magnification is, for example and without limitation, 2×, 3×, or 4× as desired for a given purpose. This enhances the scanning capsule endoscope by increasing resolution using optical magnification. When the scribes are designed for the magnifying mirror, the magnification should be appropriately considered.

2. Variable Resolution and/or Variable Magnification Scanning

In an embodiment, the resolution of an axis can be controlled by the scanning optical system. This allows for higher resolution images to be generated than with existing FPA chips within the size range required of the applications. In addition, for many applications, the imaging rate (frame rate) and resolution of the images does not need to be at a fixed (e.g., video) rate. This allows the scan system to operate at variable speeds such that when triggers within the image are activated, from, for example, additional sensors within the capsule or from an operator external to the capsule, the speed of the image generation can be changed. For example, the data rate generated can be lowered when information is redundant or not of interest, and increased when specific image information is critical to the application or different from a previous scan. This increases the efficiency of the information gathering and is similar in result to image compression. In another example, a low resolution scan may be taken when the ingestible capsule is moving through the GI tract, to ensure that information regarding the portion of the GI tract through which the capsule is passing is obtained. When the capsule is not moving, the resolution can be ramped up to obtain higher resolution images of the location. In yet another example, each color may be imaged in either high resolution or low resolution depending on a previous scan and a threshold of difference from the previous scan.

Under the variable resolution scanning approach, a slower scan can be used to produce a higher resolution image on the scanning axis. The use of a cylindrical lens (such as cylindrical lens 114) or other scanning mirror and/or prism optics provides wide angle imaging without distortion and without requiring complex optical surfaces. A radial resolution of the capsule is a function of the scan rotation rate, and is approximately equal to the line scan capture rate divided by the number of rotations per second of the scanning optics. To obtain a high resolution, for example, the capsule may capture a line scan image every degree around the viewing field. One of skill in the art will recognize that other rates of line scan image capture may be utilized without departing from the spirit and scope of the present invention. A length resolution of the capsule is a function of the linear velocity of the capsule (such as the rate at which the capsule moves through the GI tract), and is approximately equal to the number of rotations per second of the scanning optics divided by the linear velocity.

By using discrete frequency illumination, each scan can be used to collect the different reflectivity of the target surface, and therefore can be used to generate full color images and spectral analysis data at various resolutions.

Such a technique may also be used to vary the magnification of an image without any modifications to the detector. That is, if the spot size decreases while resolution stays constant, an increase in magnification results.

3. Photosensor Construction and Image Data Format

Figure 9A:
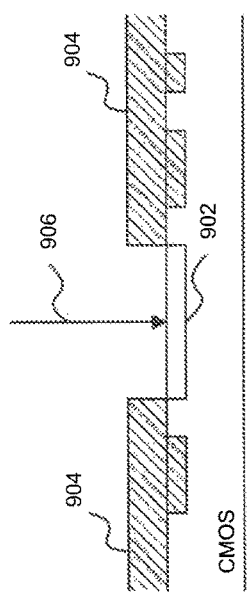
FIG. 9A is a cross-section of a photodiode.
Figure 9B:
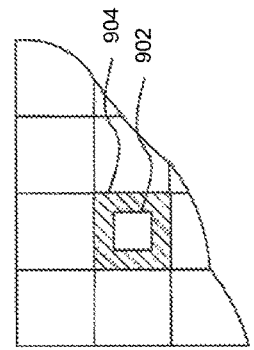
FIG. 9B is a top-down view of the photodiode of FIG. 9A.

The top surface of a typical integrated circuit, including a focal plane image sensor, has nearly complete metal coverage. This metal is required to provide addressing, data readout, as well as cell, or pixel, transistor circuit connections. Each pixel's photodiode (that is, light sensor) must be placed in an area where incoming light can reach it. FIG. 9A is an illustration of a cross-section of a typical photodiode. A photosensor 902 is implemented in CMOS. As the supporting electronics are designed depending on the characteristics of photosensor 902, they are implemented on the chip after the implementation of photosensor 902. Supporting electronics for photosensor 902 are illustrated as electronics 904. Incoming light beam 906 enters through a hole in electronics 904 so as to be incident on photosensor 902. Because of the space needed for electronics 904, the majority of the pixel area under electronics 904 cannot be used for light sensing. This limits the available light sensitivity as well as the resolution of photosensor 902. Dark current and coupled noise further limits the sensitivity of the photosensor 902. This disparity between the size of photosensor 902 and the size of a pixel containing photosensor 902 is illustrated in FIG. 9B, which is a top-down view of a portion of an exemplary photosensor array.

Large image sensors for a given pixel density have been used to provide image resolution and light sensitivity. However, the dark current and coupled noise is a tradeoff limitation of current image sensors. Additionally, this results in a significant amount of illumination that must be supplied by LED light sources on the pill, and thus a portion of the pill's battery capacity is required for it.

Figure 10A:
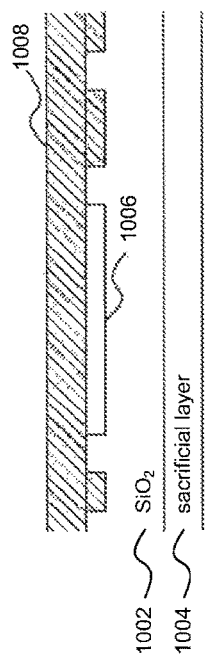
FIGS. 10A and 10B illustrate construction of a back-lit scanner according to an embodiment of the present invention.
Figure 10B:
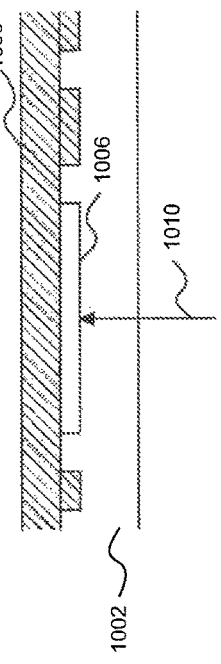

In an embodiment, a Silicon-on-Insulator (SOI) CMOS image scanner may be illuminated from the back of the integrated circuit to achieve a maximum light sensitivity and finest image resolution, while enabling a small image scanner integrated circuit. FIGS. 10A and 10B illustrate how such a back-lit scanner may be constructed. As shown in FIG. 10A, a base 1002 of silicon oxide ($SiO_2$) is implemented in place of traditional CMOS. A sacrificial metal layer 1004 is also included to provide support for base 1002. Photosensor 1006 and supporting electronics 1008 are implemented as usual, with no hole being included in electronics 1008 for accessing photosensor 1006.

Figure 10C:
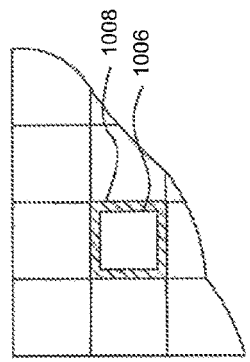
FIG. 10C is a top-down view of a photosensor array using the scanner of FIGS. 10A and 10B.

As shown in FIG. 10B, once sacrificial layer 1004 is removed, a light beam 1010 may be incident on photosensor 1006 through transparent base 1002. Because the size of photosensor 1006 is no longer limited by the area requirements for supporting electronics 1008, photosensor 1006 can be made larger, as illustrated in FIG. 10C, which is a top-down view of an exemplary photosensor array. Indeed, photosensor 1006 can be made large enough to have double digit electron sensitivity or less.

This integrated circuit technology makes it possible to capture high resolution peripheral scanned images through hemispherical optics with lower image data along the center line of the optics, in accordance with an embodiment of the present invention. On-chip image scanner circuitry may also be incorporated with variable resolution in an embodiment of the present invention to trade-off resolution with the quantity of data under electronic control.

In an embodiment, optimized circuit design and layout is performed in defining the electronic arrangement of the pixel circuitry and pixel photo sensor diodes. The photosensor diodes may be substantially arranged in a circular pattern for scanning the illuminated hemispherical field of view. The hemispherical optics (such as a fisheye lens or cylindrical lens) may work in conjunction with the image scanner layout. This arrangement offers scanning information capture and output of the image in a radial data format. In an embodiment, the outer periphery of the scanning radius contains a higher density of pixels than the center, which has the lowest pixel count per unit area of silicon by simple geometry. This provides the highest resolution on the sidewall of the intestine at or near the endoscopic capsule, while lower resolution is provided down the intestinal tract. The read-out electronics may be located primarily in the center of the array where the readout lines are the shortest for low power operation. A low density of pixels may be located throughout the readout electronic region for coverage in the center of the hemispherical scanned image which looks down the intestinal tract. The four corners may also used for image electronics, since there are no pixels located there.

In an embodiment, three dimensional data is derived by combining multiple images, especially those that form opposite ends of the capsule. Post-processing of this combined data may be performed for areas of interest by the physician's desk. Once an area of interest is selected, the data may be processed and viewed at the operator's command. Three dimensional viewing modes may be similar to fly-over map viewing having controls for elevation and azimuth.

Further regarding this embodiment, the primary data format has 0 to 360 degrees around the pill plotted on the conventional x-axis and distance down the intestine plotted on the conventional y-axis. This data format may be presented on a single page so that the entire intestine can be observed quickly as a full page thumbnail. From this view, a mouse may be used to zoom in on areas of interest (e.g., from operator observation or selection of areas of interest can be computer-assisted). Higher resolution data may be zoomed in for regions of interest. In these regions, three dimensional enhancement that may be viewed in a fly-over mode employs a similar effectiveness to fly-over map controls. Location information can be presented in combination with selection of areas of interest. These and many other data presentation modes are an outcome of image scanning, as opposed to conventional movie picture imaging. Post-processing may be employed to render this data into a more conventional format of looking down the intestine so that normal data output is available.

To limit the data for lower resolution pictures and to increase the light sensitivity, groups of pixels may be combined in the low resolution mode. This pixel combination can be performed on the array or during processing external to the array. For instance, groups of four or more neighboring pixels may be combined. Similarly, image data compression may be performed by examining the neighboring pixels electronically. In a specific example not meant to limit the present invention, a low resolution 320×320=100 k pixel frame may become a 640×640=400 k pixel frame with a 4× magnified image resolution. In this example, a 16× image magnification is 1280×1280=1.6M pixel frame. Further according to this example, a 64× magnification renders 2560×2560=6.5M pixel resolution. Due to the image scanning technology described above, the data out before data compression is about one-fourth that of a conventional imager. The excessively high amount of data output for a full scan in the highest resolution mode may be limited by smart sensor technology in the capsule electronic controls.

In an embodiment of the present invention, electrical potentials related to peristalsis may be sensed differentially from electrodes near either end of the capsule. These electrodes may also be used to load data, electronically test, sense ingestion, and turn the capsule off or on independently. Additionally, as will be described further below, intestinal pressure waveform data can be used to determine movement of the capsule. In this manner and according to a further embodiment of the present invention, under program control the scanner may gather a low resolution image data during peristalsis and progress to stages of higher resolution scanning while the local area of the intestinal tract is quiet. The use of these high resolution modes can be used to examine parts of the intestine on the cellular level where some forms of pre-cancer have been observed.

In an embodiment, after these engineering features are implemented on the SOI CMOS semiconductor chip, completed wafers may be fabricated on the semiconductor processing line. As an additional final manufacturing step, the substrate on which the SOI wafer is constructed may be removed down to the buried Oxide (BOX). In an embodiment, this yields a cellophane-like semiconductor which may be "flip-chip" mounted on the focal plane area of a PC-board or flex circuit in the capsule.

For a full spherical image scanner, both ends of the capsule may contain one of these image scanners with its respective optics.

4. Arbitrary Sampling Scanner

Scanning systems such as facsimile machines have a specifically defined resolution coordinating to the data they acquire, which is typically defined by the spot size or pixel size of the imaging array. It is possible to sub-sample the optical pixel to acquire higher resolution. In digital systems, this is typically done by utilizing more discrete pixels than optical spots, thereby requiring a higher photodetection resolution than optical resolution. This is a costly and inefficient use of the pixels. The desire for higher resolution images with basic system designs has pushed the need for higher pixel counts for starring arrays such as focal plane array (FPA) CMOS or CCD imagers.

A scanner utilizing movement of the target or movement of the sensors provides the ability to utilize high response speeds to gain higher resolution data.

In an embodiment of the present invention, the analog response of a photodetector can be utilized to capture image data from an optical scanner so that the final resolution of the system is described by a combination of the optical spot size on the target surface being imaged and the amount of sub-sampling accomplished by an analog to digital (A/D) converter. Since A/D converters have the capability to sample at extremely high data rates, this allows the scanner to be arbitrary in resolution within the confines of the response speed of the photodetector and the illumination spot size of the scanner optics. As the scanner's illumination spot moves across the scanning range, its response can be much faster than the scanning rate. In this manner, the value of the signal from a high speed photodetector responds to changes in the intensity of the scanned spot as it moves within the diameter of the original spot. Plotting the response of the photodetector shows changes in the value of the detected signal corresponding to changes in the surface of the object that are much smaller than the optical spot size. This allows a high speed A/D converter to generate several sub-samples of the image before the spot has moved to cover a completely new surface area adjacent to the initial image spot. This sub-sampling ability allows higher resolution details in the object to be detected and imaged. Mapping of the changes in the sub-sampling data allows calculations of the position, size, and intensity of surface features significantly smaller than the optical spot size.

5. Video or Scanned Image Audio Content Indicator

Humans observing continuous visual data become numb to sudden, short-lived, or unexpected changes in the image. This psycho-physical reaction is part of the human eye-brain response and is a known issue with monitoring security cameras as well as reviewing continuous streams of data from instruments such as medical monitoring equipment.

Because of this, reviewing long data streams of video images from optical scanning systems for medical applications is difficult, particularly when a majority of the scans have very similar data showing normal tissue, while a small selection of scans may have indications of disease or other medical issues of key interest.

In cases where video or scanned image streams have a majority of similar content and human monitoring or reviewing is tedious, auditory signals may be used as indicators of sudden change in the image content. For example, some modern security systems utilize temporal difference filtering of images to set off alarms when there are sudden changes in the scene so as to alert security guards of possible intrusions. Similarly, medical image data can be processed to generate cues to alert a physician or observer when the scans show tissue abnormalities.

In an embodiment of the present invention, the overall intensity profile of each line or frame may be determined by utilizing the intensity of each of the color channels of the scanner. When objects within the image change the parameters of these levels, the change in intensity values may exceed the normal range for the data stream. This intensity level data may be assigned an acoustic tone value which may be for the sum of the color values. In an embodiment, a tone may be assigned for each color channel being imaged to generate a set of tones. When multiple tones are used, a chord may be established to indicate data that is within a normal specification range, while data that exceeds the normal range may be assigned tone values to generate discordant tones whose assignments may be made to indicate the amount that the data exceeds the normal data range. Tone intensities may also be used to indicate optical channel intensities, range values outside of the normal data range, or the percentage of a frame and/or region where values exceed the normal. User selection may be made to eliminate the tones indicating normal values so that data exceeding the normal data range will generate alert tones. In addition, solid tones may be replaced with specific types of music or other acoustic media where subtle changes in the sound obtain the attention of the observer and alert the observer of the event in the video image or data.

In an embodiment, the imaging system may include a feed of the scanner video or data stream to a computer, where the value setting of the feed is converted into audio signals via software. The value setting may then be passed to an audio system via cables or wireless connections. This type of data processing may be accomplished with, for example and without limitation, a microcontroller or FPGA, which may be incorporated with other components within the data stream handling electronics.

In the case of patient wearable systems such as wearable monitors, this type of audio alarm may be used to notify the patient and/or physician via, for example, cell phone or wireless link, that the monitor has identified data exceeding the normal data range limits.

In this manner, the system user can be assured to be notified of the presence of the anomaly. With individual color tone generation and anomaly size to intensity generation, unique acoustic signatures may be associated with the nature of the anomalies, further providing the physician or observer with acoustic diagnostic information. Tonal shifts in the data values provides the human observer with a second sensory input to prevent missing important events in otherwise tedious data, and allows review of data at high speeds. Further, this acoustic assignment process may be used to highlight specific images in data prior to human review, allowing the data stream to be filtered to show only the images where the data has exceeded normal values.

6. Monitoring Peristalsis

During a peristalsis contraction, a select region of the GI tract tissue is compressed by the muscle fiber contained within its structure. This compression is how the body normally moves food and waste products through the GI tract. Monitoring of peristalsis or the muscle activity with the gastric intestinal tract is critical to evaluation of the patients ability to process and move food through the body. Damage caused by disease, nerve damage, rupture or atrophy of the muscles lining the gastric intestinal tract (including the stomach) are causes of serious conditions that can be life threatening.

In an embodiment of the present invention, the ingestible endoscopic capsule can utilize peristalsis, and other muscle contractions of the GI tract, to provide data regarding the extent and nature of the contraction. Additionally, the capsule may utilize the contraction to control the functions of the pill such as powering up, transmitting data, taking images, etc.

For example, pressure sensor(s) may be used within the ingestible capsule such that these contractions are be monitored and utilized to control the timing of acoustic transmission of data and the collection of images and other sensor data. During these contractions the tissue is squeezed against the external wall of the capsule, providing the highest acoustic coupling possible and thereby the most efficient time for acoustic signals to be sent with minimal reflections from within the gastric intestinal structure. This increase in coupling allows the capsule to utilize minimal power for transmission as well as provide an enhancement in the ability to locate the position of the capsule, for example, in three dimensions from acoustic detectors placed on the patient's skin. In addition, since the capsule is not in any significant motion between contractions the continuous collection of data such as images between contractions generates data redundancy with little value to the examining physician. Therefore, the pressure provided by the contraction can also be utilized to activate the capsule's transmission system and/or initiate data collection. Along with this, images of the tissue within the GI tract that is in direct contact with the surface of the capsule provides the ability to see the tissue with minimal distortion, unlike when the tissue is relaxed and the distance from one region of the tissue is significantly different from another region within the same image.

In another embodiment of the present invention, monitoring of the activity within the gastric system is accomplished using an ingestible capsule sensor to detect electrical signals corresponding to muscular contractions associated with peristalsis. Detecting electrical emissions from nearby muscle activity and communicating the information via an acoustical link to sensors mounted on the skin of the patient allows both a detailed analysis of the peristalsis function of the gastric intestinal tract and a 3 dimensional map of the location of the pill as it collects data to be provided. This provides physicians with the location and extent of functional anomalies within this system.

The capsule peristalsis sensor may contain electrical field sensors such as those used in EKG and muscle activity sensors in other biological monitors. The capsule may process these electrical signals and use an onboard microcontroller to modulate a piezoelectric crystal also contained along with a battery power source within the capsule. As described above, the modulated acoustic signal from the capsule containing the electrical muscle activity data is then received by acoustic sensors contained within patches on the skin of the patient. These patches may be distributed across the body in such a manner as to provide a three dimensional location of the pill as it is transmitting. An exemplary method and system for locating an ingestible sensor is further described in U.S. patent application Ser. No. 11/851, 179, filed Sep. 6, 2007, which is incorporated by reference herein in its entirety. Various embodiments of this sensor approach can combine other sensors including imaging.

Once the location is known, scanned images may be combined with more traditional data to provide a more detailed understanding of the scanned images. For example, scanned images may be combined with data from a traditional magnetic resonance imaging (MRI) procedure or from a traditional ultrasound.

CONCLUSION

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below. It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An ingestible scanning device, comprising:
   an ingestible capsule housing having a transparent window;
   a plurality of photosensors arranged to extend across a diameter of the ingestible capsule housing and to be perpendicular to a longitudinal axis of the ingestible capsule housing to form a single-axis photo-sensing array located within the ingestible capsule housing;
   a mirror located within the ingestible capsule housing and oriented to reflect an image from a surface outside the transparent window to the single-axis photo-sensing array;
   a light source configured to illuminate the surface outside the transparent window; and
   a cylindrical lens, between the single-axis photo-sensing array and the mirror, arranged to have a curvature perpendicular to the longitudinal axis of the ingestible capsule housing,
   wherein a relative position of the cylindrical lens to the single-axis photo-sensing array is moveable to sequentially focus the image onto the single-axis photo-sensing array.

2. The ingestible scanning device of claim 1, wherein the mirror is rotatable.

3. The ingestible scanning device of claim 2, further comprising an adjustable-speed motor coupled to the mirror.

4. The ingestible scanning device of claim 3, wherein an achievable resolution of a scanned axis and a speed of imaging is adjustable by adjusting a speed of the adjustable-speed motor.

5. The ingestible scanning device of claim 1, wherein the mirror is a cylindrically symmetrical reflective element or is an element combining reflective and refractive surfaces.

6. The ingestible scanning device of claim 1, further comprising a toroidal lens located around the single-axis photo-sensing array, the toroidal lens being oriented to direct light from the light source onto the mirror.

7. The ingestible scanning device of claim 1, wherein the light source is located within the ingestible capsule housing.

8. The ingestible scanning device of claim 1, wherein the light source is attached to an outer surface of the ingestible capsule housing.

9. The ingestible scanning device of claim 1, wherein the light source is a light emitting diode.

10. The ingestible scanning device of claim 1, wherein the light source is a light distribution ring.

11. The ingestible scanning device of claim 10, wherein the light distribution ring is configured to output light around approximately a perimeter of the ingestible capsule housing.

12. The ingestible scanning device of claim 1, wherein the single-axis photo-sensing array is capable of being read a line at a time.

13. The ingestible scanning device of claim 1, wherein the relative position is moveable to sequentially focus light from different regions of the image onto the single-axis photo-sensing array.

14. The ingestible scanning device of claim 1, wherein the cylindrical lens is moveable to sequentially focus light from the image onto the single-axis photo-sensing array.

15. The ingestible scanning device of claim 1, wherein the single-axis photo-sensing array is moveable to sequentially focus light from the image onto the single-axis photo-sensing array.

* * * * *